「12) United States Patent
Vente et al.

(10) Patent No.: US 12,325,632 B2
(45) Date of Patent: Jun. 10, 2025

US012325632B2

(54) PRODUCTION OF CARBON DIOXIDE AND AMMONIA FROM RESIDUAL GASES IN THE STEEL AND METAL INDUSTRIES

(71) Applicant: Nederlandse Organisatie voor toegepast-natuurwetenschappelijk Onderzoek TNO, The Hague (NL)

(72) Inventors: Jaap Ferdinand Vente, The Hague (NL); Vasileios Sfakianakis, The Hague (NL); Paul Dean Cobden, The Hague (NL)

(73) Assignee: Nederlandse Organisatie voor toegepast-natuurwetenschappelijk Onderzoek TNO, The Hague (NL)

( * ) Notice: Subject to any disclaimer, the term of this patent is extended or adjusted under 35 U.S.C. 154(b) by 1089 days.

(21) Appl. No.: 17/264,343

(22) PCT Filed: Aug. 2, 2019

(86) PCT No.: PCT/EP2019/070940
§ 371 (c)(1),
(2) Date: Jan. 29, 2021

(87) PCT Pub. No.: WO2020/025815
PCT Pub. Date: Feb. 6, 2020

(65) Prior Publication Data
US 2021/0292163 A1    Sep. 23, 2021

(30) Foreign Application Priority Data
Aug. 2, 2018 (EP) .................................. 18187053

(51) Int. Cl.
*C01B 3/02* (2006.01)
*C01B 3/16* (2006.01)
*C01C 1/04* (2006.01)

(52) U.S. Cl.
CPC ............... *C01B 3/025* (2013.01); *C01B 3/16* (2013.01); *C01C 1/0488* (2013.01); *C01B 2203/0233* (2013.01); *C01B 2203/042* (2013.01); *C01B 2203/0445* (2013.01); *C01P 2006/80* (2013.01)

(58) Field of Classification Search
CPC ... C01B 3/025; C01B 3/16; C01B 2203/0233; C01B 2203/042; C01B 2203/0445; C01C 1/0488; C01P 2006/80; C21B 5/06; C21B 2100/80; Y02P 10/122; Y02P 10/143; Y02P 10/25; Y02P 20/52; Y02P 20/582; Y02P 30/00; C07C 273/10
See application file for complete search history.

(56) References Cited

U.S. PATENT DOCUMENTS

| 3,872,025 | A | 3/1975 | Singleton |
| 6,190,632 | B1 | 2/2001 | Shah et al. |
| 2017/0210703 | A1* | 7/2017 | Meißner ................. C01B 3/025 |
| 2018/0036672 | A1* | 2/2018 | Sundaram .......... B01D 53/0473 |

FOREIGN PATENT DOCUMENTS

| WO | 2010059055 A1 | 5/2010 |
| WO | 2015086149 A1 | 6/2015 |
| WO | 2016135572 A1 | 9/2016 |
| WO | 2017121817 A1 | 7/2017 |

OTHER PUBLICATIONS

Boon et al. "Comparison of the efficiency of carbon dioxide capture by sorption-enhanced water-gas shift and palladium-based membranes for power and hydrogen production". International Journal of Greenhouse Gas Control 50 (2016) 121-134 (Year: 2016).*

* cited by examiner

*Primary Examiner* — Wayne A Langel
*Assistant Examiner* — Syed T Iqbal
(74) *Attorney, Agent, or Firm* — N.V. Nederlandsch Octrooibureau

(57) ABSTRACT

The present invention relates to a process for the production of carbon dioxide and ammonia for the production of urea or ammonium carbamate from residual gases in the steel and metal industries, in particular basic oxygen furnace (BOF) gas and/or blast furnace (BF) gas. The process according to the invention comprises: (a) subjecting a mixture comprising (i) basic oxygen furnace gas and/or blast furnace gas and (ii) steam to a separation-enhanced water gas shift reaction to obtain a first product gas comprising $H_2$ and $N_2$ and a second product gas comprising $CO_2$; (b) subjecting the first product gas originating from step (a) to $NH_3$ synthesis to obtain a product gas comprising $NH_3$; and (c) optionally subjecting at least part of the $CO_2$ originating from step (a) and at least part of the $NH_3$ originating from step (b) to the synthesis of urea or ammonium carbamate.

14 Claims, No Drawings

PRODUCTION OF CARBON DIOXIDE AND AMMONIA FROM RESIDUAL GASES IN THE STEEL AND METAL INDUSTRIES

FIELD OF THE INVENTION

The present invention relates to a process for the production of urea or ammonium carbamate from residual gases in the steel and metal industries, in particular basic oxygen furnace (BOF) gas and/or blast furnace (BF) gas.

BACKGROUND ART

Yearly, over 190 million tons of urea ($NH_2$—CO—$NH_2$) are produced on a huge scale. 80-90% of this urea is used as fertilizer, although many other applications exist. The worldwide demand for fertilizer is expected to increase steadily over the coming years, and so will the demand for urea. Industrially, urea is produced from ammonia and carbon dioxide, and employs two equilibrium reactions:

$$2NH_3 + CO_2 \leftrightarrow H_2NCOONH_4 \quad (1)$$

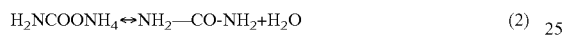

$$H_2NCOONH_4 \leftrightarrow NH_2\text{—}CO\text{-}NH_2 + H_2O \quad (2)$$

Conventional urea synthesis mostly occurs in the vicinity of ammonia plants, where carbon dioxide is produced as by-product of ammonia synthesis from coal, natural gas or other hydrocarbons. Ammonia and carbon dioxide are then subjected to the Bosch-Meiser urea process to produce urea according to reactions (1) and (2). The raw material of urea are thus fossil fuels such as natural gas or coal. WO 2015/086149 discloses a method for the production of ammonia and $CO_2$ for the synthesis of urea, wherein metallurgical gas (originating from the blast furnace, cokes oven or converter) is subjected to a gas purification step and subsequently a water gas shift reaction and gas separation into a gas containing $N_2$ and $H_2$ and a gas containing $CO_2$. The first is subjected to ammonia synthesis, while the second gas is subjected to multi-stage $CO_2$ separation in order to obtain a gas sufficiently high in $CO_2$ to enable urea synthesis.

The worldwide yearly production of ammonium carbamate is much lower, but occurs very similarly to the production of urea. Here, only equilibrium reaction (1) plays a role, wherein two molecules of ammonia and one molecule of carbon dioxide are converted in one molecule of ammonium carbamate. Ammonium carbamate has found some niche application, but is mainly formed as intermediate in the production of urea.

Conventional urea and ammonium carbamate production heavily relies on the use of fossil fuels such as natural gas or coal. Although some developments have been made in using residual gases, there remains a need in the art for an energy- and cost-efficient process for the production of urea and ammonium carbamate wherein the use fossil fuels is no longer required. The present invention provides in this need.

SUMMARY OF THE INVENTION

The inventors have developed a process for the production of carbon dioxide and ammonia for the production of urea or ammonium carbamate, wherein BOF gas, BF gas or a mixture thereof is used as carbon source. The present process not only provides a valuable use of gases that are typically considered waste or burned for fuel and diminishes the reliance on fossil fuels, it greatly reduces $CO_2$ emissions and any $CO_2$ is obtained in a sequestration-ready state. The process according to the invention comprises the following steps:

(a) subjecting a mixture comprising (i) basic oxygen furnace gas and/or blast furnace gas and (ii) steam to a separation-enhanced water gas shift reaction to obtain a first product gas comprising $H_2$ and $N_2$ and a second product gas comprising $CO_2$;

(b) subjecting the first product gas originating from step (a) to $NH_3$ synthesis to obtain a product gas comprising $NH_3$.and (c) optionally subjecting at least part of the $CO_2$ originating from step (a) and at least part of the $NH_3$ originating from step (b) to the synthesis of urea or ammonium carbamate.

Preferred embodiments of the process according to the invention are listed here below:

1. Process for the production of carbon dioxide and ammonia for the production of $H_2NC(O)X$, wherein $X=NH_2$ or $O^-\ NH_4^+$, comprising:
   (a) subjecting a mixture comprising (i) basic oxygen furnace gas and/or blast furnace gas and (ii) steam to a separation-enhanced water gas shift reaction to obtain a first product gas comprising $H_2$ and $N_2$ and a second product gas comprising $CO_2$;
   (b) subjecting the first product gas originating from step (a) to $NH_3$ synthesis to obtain a product gas comprising $NH_3$; and
   (c) optionally subjecting at least part of the $CO_2$ originating from step (a) and at least part of the $NH_3$ originating from step (b) to the synthesis of $H_2NC(O)X$.

2. The process according to embodiment 1, wherein the process is for the production of $H_2NC(O)X$ and wherein step (c) is performed.

3. The process according to embodiment 2, wherein the molar ratio $NH_3$ to $CO_2$ in the feed of step (c) is in the range of 2-4, preferably by using all of the $NH_3$ originating from step (b) and part of the $CO_2$ originating from step (a).

4. The process according to any one of the previous embodiments, wherein the remainder of the second product gas originating from step (a) is subjected to $CO_2$ sequestering.

5. The process according to any one of the previous embodiments, wherein $X=NH_2$.

6. The process according to any one of the previous embodiments, wherein in case the first product gas originating from step (a) comprises CO and $CO_2$, it is subjected to methanation to convert CO and $CO_2$ into $CH_4$, prior to being subjected to step (b).

7. The process according to any one of the previous embodiments, wherein the $H_2$ to $N_2$ molar ratio in the first product stream that is subjected to step (b) is set to about 3 by addition of $H_2$ or $N_2$.

8. The process according to embodiment 7, wherein 0-10 mol % $H_2$ is added to the first product gas prior to step (b), based on the molar content of $H_2$ in the first product gas.

9. The process according to any one of the previous embodiments, wherein the water gas shift reaction of step (a) is sorption-enhanced.

10. The process according to any one of the previous embodiments, wherein the mixture comprises BOF gas and/or BF gas, wherein 0-15 wt % or 50-100 wt % is BF gas, and the remainder is BOF gas.

11. The process according to any one of the previous embodiments, wherein a pre-shift step is performed prior to step (a), wherein the mixture is subjected to a water gas shift reaction that is not separation-enhanced before being subjected to step (a).
12. The process according to any one of the previous embodiments, wherein step (a) involves:
    (a1) contacting the incoming gas with a sorbent capable of adsorbing $CO_2$, under conditions suitable to convert CO and $H_2O$ in $H_2$ and $CO_2$, to obtain a first product gas comprising $H_2$ and $N_2$, and a sorbent loaded with $CO_2$; and
    (a2) regenerating the loaded sorbent to obtain a second product gas comprising $CO_2$.
13. The process according to any one of the previous embodiments, wherein the electricity needed to perform the process is obtained from renewable resources.
14. The process according to any one of the previous embodiments, wherein step (b) involves:
    (b1) providing a reaction mixture comprising the first product gas originating from step (a);
    (b2) subjecting the reaction mixture to the equilibrium reaction in a reactor or sequence of reactors, to obtain a reactor outlet mixture comprising the comprising $NH_3$ and at least one of the reactants;
    (b3) regenerating the loaded sorbent obtained in step (b5) by flushing the loaded sorbent with the reactor outlet mixture originating from step (b2), to obtain regenerated sorbent and an effluent comprising desorbed product $NH_3$;
    (b4) separating the effluent originating from step (b3) into a product stream comprising $NH_3$ and a reactant stream comprising $N_2$, $H_2$ and $NH_3$;
    (b5) a sorption step, wherein
        (i) the reactant stream originating from step (b4); and/or
        (ii) an intermediate reactor mixture, which is obtained at the outlet of a reactor not being the last reactor of the reactor sequence, prior to being subjected to the subsequent reactor of the reactor sequence,
    is subjected to an sorption step by contacting with a sorbent selective for $NH_3$, wherein the sorbent is not capable of sorbing $N_2$ and $H_2$, to obtain a sorbent loaded with $NH_3$ and a depleted mixture comprising $N_2$ and $H_2$ that in case step (b5) is performed on the intermediate reactor mixture, is subjected to the subsequent reactor of the reactor sequence.

DETAILED DESCRIPTION

The process according to the invention is for the production of carbon dioxide and ammonia for the production of $H_2NC(O)X$, wherein $X=NH_2$ or $O^- NH_4^+$, and comprises:
(a) subjecting a mixture comprising (i) basic oxygen furnace gas and/or blast furnace gas and (ii) steam to a separation-enhanced water gas shift reaction to obtain a first product gas comprising $H_2$ and $N_2$ and a second product gas comprising $CO_2$;
(b) subjecting the first product gas originating from step (a) to $NH_3$ synthesis to obtain a product gas comprising $NH_3$.and
(c) optionally subjecting at least part of the $CO_2$ originating from step (a) and at least part of the $NH_3$ originating from step (b) to the synthesis of $H_2NC(O)X$, wherein $X=NH_2$ or $O^- NH_4^+$.

Herein, the product gas originating from a certain step may also be referred to as the product gas of a certain step. The product of the process according to the present invention may be carbon dioxide and ammonia for the production of urea or ammonium carbamate, or may be urea or ammonium carbamate. Herein, "urea or ammonium carbamate" may also be referred to as $H_2NC(O)X$, wherein $X=NH_2$ or $O^- NH_4^+$. In one embodiment, the process is for the production of carbon dioxide and ammonia, which is suitable for the production of $H_2NC(O)X$, wherein $X=NH_2$ or $O^- NH_4^+$, and in this embodiment step (c) is not performed. In one embodiment, the process is for the production of urea or ammonium carbamate, and step (c) is performed. In one embodiment, the process is for the production of urea and $X=NH_2$. In an alternative embodiment, the process is for the production of ammonium carbamate and $X=O^- NH_4^+$.

Basically, the invention concerns the use of the separation-enhanced water gas shift in the production of a $H_2/N_2$ stream and a $CO_2$ stream from basic oxygen furnace (BOF) gas and/or blast furnace (BF) gas. The inventors found that the use of the separation-enhanced water gas shift reaction is especially suited in this respect, as it affords a first product stream comprising $H_2$ and $N_2$ in a molar ratio of close to 3, the optimal ratio for ammonia production, and a second product stream concentrated in $CO_2$, which is ideally suited to be used in the synthesis of urea or ammonium carbamate.

The process according to the invention makes efficient use of streams (BF gas and/or BOF gas) that are currently considered waste or are inefficiently used as fuel. In the present process, these streams are used as precursor for urea or ammonium carbamate. Concomitant with the production of 1 ton urea on the basis of natural gas, about 0.3 ton of $CO_2$ is emitted to the environment as a diluted stream, mostly coming from the off-gases of the primary reformer. As a consequence approximately 72% of the carbon coming from the methane is incorporated into the urea. Using the process according to the present invention, about 25% of the carbon originating from BOF gas is incorporated into the urea, depending on the exact composition of the incoming gas. The remainder becomes available as sequestration-ready $CO_2$. The $CO_2$ emission of conventional urea production and BOF gas burning to produce electricity is estimated to be 3.3 ton $CO_2$ per ton urea formed. Converting 0.35 ton of $CH_4$ into 1 ton of urea gives rise to the emission of about 0.3 ton $CO_2$ (see reaction (3a) below). Together with electricity production from BOF gas containing a total amount of carbon equivalent to 3.0 ton $CO_2$ (see reaction (3b) below) gives a total of 3.3 ton $CO_2$. In the process according to the invention, urea is manufactured on the basis of the same amount of BOF gas, giving 1 ton urea and 2.2 ton $CO_2$ (see reaction (4) below). Any required electricity may be generated by renewable sources such as wind and solar, giving no, or very small, $CO_2$ emission. Total reduction in $CO_2$ formation thus already amounts to 1.1 ton per ton urea formed or 33%. In addition, the remaining $CO_2$ of the process according to the invention is in the form of a concentrated $CO_2$ stream originating from the separation-enhanced water gas shift reaction of step (a), which is in a sequestration-ready state, while in the conventional urea production and BOF gas burning, $CO_2$ is obtained in diluted form and is emitted to the environment. Thus, potentially, the $CO_2$ emission from urea production can be reduced to zero using the process according to the invention.

(3a) 0.4 ton $CH_4 \rightarrow$ 1 ton urea+0.3 ton $CO_2$
(3b) 3.0 ton BOF gas ($CO_2$ equivalents)$\rightarrow$electricity+3.0 ton $CO_2$ (dilute)

(4) 3.0 ton BOF gas (CO$_2$ equivalents)→1 ton urea+2.2 ton CO$_2$ (storage-ready)

Notably, the above calculations are based on the embodiment wherein pure BOF gas is used as starting material. However, similar results are obtained with BF gas or mixtures of BOF gas and BF gas as starting material. The process according to the invention thus provides a striking reduction in CO$_2$ emission and utilizes off-gases that are currently merely burned for electricity. In addition, the process according to the invention enables the production of urea or ammonium carbamate without the need of methane as precursor, as such reducing the reliance on natural gas. In order to further increase the environmentally friendly nature of the process according to the invention, it is preferred that any energy and electricity needed to perform the process according to the invention is obtained from renewable resources as known in the art. Finally, the remaining CO$_2$ becomes available as sequestration-ready without any further treatment needed, thus reducing the overall cost of carbon capture and sequestration in the steel industry.

The Incoming Gas

A typical steel making process in an integrated steel mill furnishes three residual gases, which originate from the blast furnace (BF gas), the cokes oven (CO gas) and the basic oxygen furnace (BOF gas). The process according to the present invention employs BOF gas, BF gas or a mixture thereof to produce ammonia and CO$_2$ for the production of urea or ammonium carbamate. BOF gas typically comprises or even consists of CO, CO$_2$, N$_2$ and optionally H$_2$.

In one embodiment, the compositions of BOF, BF and CO gases are defined according to the following table (in vol % or mol %).

| Component | BOF gas General | BOF gas Preferred | BF gas General | BF gas Preferred | CO gas General | CO gas Preferred |
|---|---|---|---|---|---|---|
| CO | 50-65 | 55-60 | 15-30 | 20-25 | ≤10 | 2-6 |
| CO$_2$ | 14-26 | 17-23 | 15-30 | 20-26 | ≤10 | 1-5 |
| H$_2$ | ≤10 | 1-5 | ≤10 | 2-6 | 50-70 | 56-66 |
| N$_2$ | 10-30 | 15-25 | 40-60 | 45-65 | ≤12 | 3-10 |
| CH$_4$ | ≤5 | ≤1 | ≤5 | ≤1 | 15-35 | 20-30 |
| Other * | ≤5 | ≤1 | ≤5 | ≤1 | ≤5 | ≤1 |

In the above table, * indicates the total content of other components. These compositions may differ from location to location, plant to plant, and may change overtime. This is especially true for the non-continuous process of the convertor of basic oxygen furnace. These compositions are therefore time and location average values with large uncertainty. Currently, BOF and BF gases are combusted to produce electricity, which is in terms of CO$_2$ pollution an even worse alternative than using coal to produce electricity. The process according to the invention provides a more environmentally friendly use of BOF and BF gas, in the production of urea or ammonium carbamate. Step (a) employs either BOF gas, BF gas or a mixture thereof. This is also referred to as the "incoming gas". In other words, BOF gas and/or BF gas is subjected to step (a). The content of BOF gas in the mixture of BOF gas and BF gas may thus range from 0% to 100%, wherein 0% represents pure BF gas and 100% represents pure BOF gas. In one embodiment, the mixture of BOF gas and BF gas contains 0-15 wt %, preferably 0-10 wt %, BF gas, and the remainder is BOF gas. In one embodiment, the mixture of BOF gas and BF gas contains 10-70 wt %, preferably 20-60 wt %, BF gas, and the remainder is BOF gas. In one embodiment, the mixture of BOF gas and BF gas contains 50-100 wt %, preferably 60-100 wt %, BF gas, and the remainder is BOF gas. In a preferred embodiment, the mixture comprises BOF gas and/or BF gas, wherein 0-15 wt % or 50-100 wt %, preferably 0-10 wt % or 60-100 wt %, is BF gas, and the remainder is BOF gas. The inventors have established that the process according to the invention is economically favourable, in that the costs for urea production are about the same as for conventional urea production, although with many advantageous in terms of the environment. However, for the embodiments wherein the mixture comprises BOF gas and/or BF gas, wherein 0-15 wt % or 50-100 wt %, preferably 0-10 wt % or 60-100 wt %, is BF gas, and the remainder is BOF gas, the costs of the process according to the invention are even lowered compared to conventional urea production. In one embodiment, the incoming gas contains at least BOF gas, preferably the incoming gas contains only BOF gas and substantially no BF gas. In other words, in a particularly preferred embodiment, the incoming gas is BOF gas. Additionally or alternatively, it is preferred that the incoming gas has a high content of carbon oxide species (CO+CO$_2$), such as at least 70 wt % or even 75-90 wt %.

Because BF gas and BOF gas are available from the same site (e.g. a steel mill), they are readily combined in the mixture that is subjected to step (a). The ratio wherein BF gas and BOF gas are combined provides the process with a surprising flexibility. Even in situations wherein these gases are not available continuously, depending on the exact operating conditions of the steel mill, the process according to the invention still operates smoothly. Further, since the use of BF gas lowers the CO to CO$_2$ ratio in the mixture, which may negatively impact the equilibrium of the water gas shift process, some hydrogen gas can be added to the mixture prior to step (a). As such, the gas originating from step (a) still contains sufficient hydrogen gas for the NH$_3$ synthesis of step (b) to occur. Alternatively or additionally, if needed some additional hydrogen gas is mixed with the gas originating from step (a) upstream of step (b). In order to maintain the renewable nature of the process, any additionally added hydrogen gas is preferably from a renewable source. Even though the possibility of adding hydrogen gas may serve to improve the flexibility of the process, e.g. in situations wherein BOF gas is only limited available, such addition is typically not required in order for the process to operate smoothly. Hence, in one embodiment, no hydrogen gas is added to the mixture that is subjected to step (a). Likewise, in one embodiment, no hydrogen is added to the gas originating from step (a) prior to step (b).

Step (a): Separation-Enhanced Water Gas Shift

In step (a), a mixture of the incoming gas and steam is subjected to a separation-enhanced water gas shift reaction. Herein, the incoming gas is contacted with a catalyst capable of catalysing the water gas shift reaction. The water gas shift reaction is the forward reaction in the following equilibrium:

$$CO+H_2O \leftrightarrow H_2+CO_2 \qquad (5)$$

BOF and BF gas contains about 50 wt % (for BF gas) or even 80 wt % (for BOF gas) carbon oxide species (CO+CO$_2$) and is very low in H$_2$, and the inventors surprisingly found that such a gas could be successfully shifted in a water gas shift reaction. Such high carbon oxide species content are not typically studied as incoming gas of a water gas shift reaction, since typical levels that would be employed in the context of electricity production are as low as 10 to 20%. Further, high partial CO$_2$ pressures in the incoming gas would be expected to lead to increased formation of complexes on the surface of the sorbent (see Boon et al., *Chem. Eng. J.* 2014, 248, 406-414). The inventors unexpectedly found that the process ran smoothly under these demanding conditions. Due to the abundance of CO in BOF gas and the addition of steam, the forward reaction is favoured and $H_2$ and $CO_2$ are formed in step (a). Furthermore, in the separation-enhanced water has shift reaction, $CO_2$ is separated from the remaining components and removed from the gas phase equilibrium, e.g. by adsorption on the catalyst. The inventors have realized that employing water gas shift reaction in separation-enhanced mode provides the advantage that two product gases are obtained wherein $H_2/N_2$ are substantially separated from $CO_2$. As such, the separation-enhanced water gas shift reaction was found ideally suited in the formation of ammonia and $CO_2$ for the production of urea or ammonium carbamate from BOF gas and/or BF gas.

"Separation-enhanced" refers to the separation of one of the products from the equilibrium mixture, such that the equilibrium shifts towards the products. For the water gas shift of step (a), this means that that either $H_2$ or $CO_2$, is separated from the equilibrium mixture. Suitable means to accomplish separation-enhancement include the use of selective membranes and selective adsorbents. For example, the water gas shift of step (a) is performed in sorption-enhanced mode, wherein $CO_2$ is adsorbed onto a $CO_2$-selective adsorbent and the equilibrium mixture emerging from step (a) contains mainly $H_2$. Preferably, step (a) is performed in sorption-enhanced mode. Sorption-enhanced water gas shift reactions are known in the art. For the sorption-enhanced water gas shift reaction, a water gas shift catalyst is combined with an adsorbent for selective adsorption of $CO_2$, which activities are preferably combined in a single material.

The steam subjected to step (a) is used to achieve several effects: to accomplish reaction during a pre-shift (see below), to accomplish reaction during sorption-enhanced water gas shift, and optionally for rinsing and purging. Preferably, such a steam rinse and/or purge is implemented, as this was found to enhance product recovery. The amount of steam that is added to the incoming gas to step (a) may depend on the exact composition, in particular the CO content, of the incoming gas. Typically, the steam content of BF and BOF gas is negligible, such that significant amounts of steam may be added to the mixture. Preferably, the amount of steam added is such that the steam content in the mixture is 1-5 times, more preferably 1.5-3, most preferably 1.8-2.5 times the CO content in the mixture. A molar ratio $H_2O$ to CO of about 2 was found to be the optimal ratio for the water gas shift reaction. Such molar ratios are especially preferred in case a pre-shift is employed.

In step (a), the incoming gas is contacted with a catalyst capable of catalysing the water gas shift reaction. Such catalysis occurs under conditions suitable to convert CO and $H_2O$ in $H_2$ and $CO_2$. Preferably, said catalyst is a sorbent capable of adsorbing $CO_2$. The equilibrium mixture that exits the water gas shift reactor is thus free from $CO_2$ and contains $H_2$ as well as $N_2$, which is comprised in BOF and BF gas and is unaffected by the water gas shift reaction. In addition to $N_2$, further inerts such as $CH_4$ may be present in the equilibrium mixture. The water gas shift reaction of step (a) further affords a $CO_2$-rich gas. This is obtained by regeneration of the loaded sorbent. Thus, in a preferred embodiment, step (a) comprises:

(a1) contacting the incoming gas with a sorbent capable of adsorbing $CO_2$, under conditions suitable to convert CO and $H_2O$ in $H_2$ and $CO_2$, to obtain a first product gas comprising $H_2$ and $N_2$, and a sorbent loaded with $CO_2$; and (a2) regenerating the loaded sorbent to obtain a second product gas comprising $CO_2$.

Upon progression of the water gas shift reaction, the sorbent becomes loaded with $CO_2$ that is formed during the reaction or already present in the incoming gas. When the sorbent is saturated, or—preferably—slightly earlier, the sorbent is regenerated to obtain a stream of desorbed $CO_2$. Regeneration of the loaded sorbent is known in the art and typically involves (i) a rinse step wherein the sorbent is flushed with a rinse gas comprising steam, (ii) one or more pressure equalization steps, (iii) a depressurization step, (iv) a purge step wherein the sorbent is flushed with a purge gas comprising steam, (v) one or more pressure equalization steps, and (vi) a repressurization step. During rinse step (i), stream replaces non-adsorbed molecules such as $H_2$ that are still present in the column, while the $CO_2$ remain adsorbed on the sorbent. Typically, the rinse gas is steam. During the pressure equalization steps (ii), the reactor is decompressed to enable recovery of $CO_2$ in steps (iii) and (iv). $CO_2$ recovery occurs in steps (iii) and (iv). In step (iii), the pressure in the reactor is reduced to ambient, during which some $CO_2$ is already desorbed from the column. Notably during steps (ii) and (iii), no gas enters the reactor. During step (iv), the sorbent is flushed with steam, during which $H_2O$ molecules replace the adsorbed $CO_2$ molecules. Typically, the purge gas is steam. The off-gas of steps (iii) and (iv) are typically combined as the second product gas of step (a). During the pressure equalization steps (v), the reactor is pressurized again until the desired pressure for step (a1) is reached. Preferably, the compression energy that is released in step (ii) is used in step (v), which can be accomplished by using multiple reactors is series.

The skilled person is acquainted with the separation-enhanced water gas shift reaction and knows what conditions should be applied in order to obtain a first product gas comprising $H_2$ and $N_2$ and adsorbed $CO_2$. For example, the temperature in the separation-enhanced water gas shift reactor may suitably be in the range of 200-550° C., preferably 300-500° C., most preferably 350-450° C. and the pressure is preferably in the range 5-500 bar, most preferably 5-50 bar. As the skilled person will understand, appropriate steps, such as heating and pressurizing, are preferably taken to ensure these conditions are met. Also, the type of sorbent that is suitably applied in step (a) is known to the skilled person and irrelevant for the functioning of the process according to the invention. Suitable sorbents may comprise mixtures of oxide, hydroxide and/or carbonate metal complexes, including optionally promoted alumina- and hydrotalcite-based materials. Preferably, one or more promotor(s) are used, more preferably the promotor(s) are independently selected from K, Na, Li, Cs, Rb, Mg, Mn, Ti, Ag, Cu, Co, Pb, Fe and Cd. In a preferred embodiment, the alumina- or hydrotalcite-based sorbent is at least alkali-promoted, and more preferably also contains a second promotor selected from the afore-mentioned group. The alkali promoter is preferably at least Na or K, most preferably at least K. The second promotor is preferably one or more of Mg, Fe and Mn. Herein, the alkali is preferably selected rom K, Na, Li, Cs and Rb. Most preferably, the sorbent comprises or even consists of alkali-promoted hydrotalcite. Preferred sorbents are disclosed in WO 2010/059055.

The mixture of the incoming gas and steam may be subjected to a pre-shift prior to being subjected to step (a), or such a pre-shift may be part of step (a). Such a pre-shift is known in the art and concerns a water gas shift reaction which is not separation-enhanced. During the pre-shift, the water gas shift equilibrium is shifted to a large extent towards the product side, such that the CO level is reduced to 1-15 mol %, typically 3-10 mol %. Such a pre-shift step is advantageously performed, as it facilitates coping with the high carbon monoxide load of the incoming gas, which may be as high as 60 wt % CO in BOF gas. A further advantage of the pre-shift resides in the heat management. The heat obtained by shifting the gas mixture towards the products of equilibrium (5), may partly be generated during the pre-shift, such that the amount of heat generated during the separation-enhanced water gas shift is lowered, and the need for heat removal is reduced.

The separation-enhanced water gas shift reaction of step (a) affords on one hand a first product gas with an optimal $H_2$ to $N_2$ molar ratio for the ammonia formation of step (b), and on the other hand a second product gas, which is already sufficiently high in $CO_2$ content to be able to produce urea or ammonium carbamate when reacted with the product of step (b). Hence, for the production of ammonia and $CO_2$ for urea or ammonium carbamate synthesis from BF gas and/or BOF gas, the use of the separation-enhanced water gas shift reaction as first step was found to be ideally suitable. The first product gas originating from step (a) may contain further gaseous species, such as inert gases like noble gases, methane and higher hydrocarbons, and possibly minor amounts of CO and $CO_2$ (slip through). Typically, the content of the species other than $H_2$ and $N_2$ is low, e.g. at most 5 wt % or even at most 2 wt %. The presence and composition of these further species highly depends on the composition of the incoming gas, and is not crucial for the functioning of the process according to the invention. The process according to the invention may contain a methanation step as discussed below, wherein the traces of CO and $CO_2$ in the first product gas is converted into methane, before it is subjected to step (b).

The second product stream originating from step (a) comprises $CO_2$, which is desorbed from the regenerated sorbent. This stream may contain further steam used in the regeneration, and sour components already present in the feed stream, e.g. $H_2S$ and COS. In one embodiment, a minor additional step is implemented to remove steam and/or sulphurous components from this stream, if those are present. As further treatment of the second product stream containing $CO_2$ will be limited and the $CO_2$ recovery required is low, a more efficient and compact process compared to prior art processes for the production of ammonia and $CO_2$ for urea or ammonium carbamate synthesis is obtained. A further advantage of the separation-enhanced water gas shift reaction includes is ability to operate under sour conditions. Thus, any $H_2S$ that may be present in the incoming gas does not jeopardize the efficacy of the process. Further, $H_2S$ is adsorbed in the sorption-enhanced water gas shift reaction and is thus removed from the first product stream and not subjected to step (b). Further polar species, such as steam, may also be present in the second product gas originating from step (a). The inventors further found that employing a separation-enhanced water gas shift reaction as step (a) provides a significant improvement over a pressure-swing adsorption to separate $CO_2$ from an incoming gas or reaction mixture also containing $H_2$ (and $N_2$.), and remaining CO. Even when a proper adsorbent is selected, pressure-swing adsorption will absorb all species present in the mixture to some extent. The second product stream would thus inevitably contain some CO, which jeopardizes the further reaction in step (c) and should thus be removed prior to such a step (c). The inventors surprisingly found that an additional CO removal step could be avoided in case a separation-enhanced water gas shift reaction was employed instead of a pressure-swing adsorption step to remove $CO_2$.

In a preferred embodiment, the second product gas originating from step (a) is subjected to a $CO_2$ concentration step or a $CO_2$ splitting step, prior to being subjected to step (c). Herein, $CO_2$ concentration may also cover purification steps, such as desulphurisation. During this step, the second product gas is further purified and split into a high-purity, chemically pure $CO_2$ stream, which is preferably subjected to step (c), and a $CO_2$ stream that is ready to be stored by $CO_2$ sequestering. Such a $CO_2$ splitting step is known in the art, and the exact parameters and conditions at which it is performed is not crucial for the operation of the process according to the invention. Typically, this step operates at a pressure of 5-25 bar.

Step (b): Ammonia Production

The first product stream of the separation-enhanced water gas shift reaction of step (a) was found to be ideally suited to be subjected to conventional ammonia synthesis. Ammonia production from a mixture of $N_2$ and $H_2$ is well-known in the art and typically occurs via the Haber process, wherein nitrogen in converted into ammonia by reaction with hydrogen, using a metal catalyst, according to equilibrium reaction (6):

$$N_2 + 3H_2 \leftrightarrow 2NH_3 \tag{6}$$

The synthesis of ammonia from a mixture of $N_2$ and $H_2$ is known to the skilled person, and the exact conditions and parameters of step (b) are not crucial for the operation of the process according to the invention. Typically, step (b) operates at 100-250 bar and 300-550° C. The feed of the ammonia reactor typically contains about 90 vol % of a recycle and only 10 vol % of the first product stream originating from step (a), containing the reactants. The recycle gas contains about 5 wt % ammonia as well as non-reacted $N_2$ and $H_2$. An equilibrium is established at about 15 wt % ammonia in the product mixture of step (b). This product mixture is typically led to a condenser, where ammonia is separated by condensation and a recycle stream is formed, containing the gaseous compounds including $N_2$, $H_2$ and some remaining ammonia.

Depending on the composition of the first product stream originating from step (a), this product stream may first be subjected to a methanation step. Substantial amounts of CO and $CO_2$ in the first product stream may be detrimental to the ammonia synthesis and is therefore preferably converted into the inert $CH_4$ via a methanation step. However preferentially, the conversion and separation during step (a) is sufficiently complete that the content of CO and $CO_2$ in the first product stream is negligible, such that no methanation step between steps (a) and (b) is required. Methanation is known in the art and can be performed in any way possible. It typically operates at a pressure in the range of 10-50 bar.

Depending on the molar ratio $H_2$ to $N_2$ in the first product stream originating from step (a), some additional $H_2$ or $N_2$ may be added to the first product stream prior to being subjected to step (b) or during step (b), e.g. in the recycle loop. Typically, the addition of some $H_2$ may be desired to achieve the optimal $H_2$ to $N_2$ ratio for step (b). The optimal $H_2$ to $N_2$ molar ratio is 3, and any deviation from this optimal ratio is preferably resolved by addition of $H_2$ or $N_2$ to the first product stream. Thus, in one embodiment, the $H_2$ to $N_2$ molar ratio in the first product stream that is subjected to step (b) is set to about 3 by addition of $H_2$ or $N_2$. In case a methanation step would be performed prior to step (b), the $H_2$ or $N_2$ is preferably added after methanation, more preferably after subjecting the product stream of the methanation step to condensation. In case $H_2$ is added to the first product stream, this $H_2$ is preferably obtained from renewable resources as known in the art, to maximize the environmental friendliness and minimize the overall $CO_2$ emission of the process according to the invention. $H_2$ may originate from CO gas, either by purification therefrom or by reforming any methane present therein, or from electrolysis using renewable electricity. A preferred source of $H_2$ is CO gas, as it is just as BOF gas and BF gas, an effluent gas of the steel industry. In case $N_2$ is added to the first product stream, this is preferably in the form of minor amounts of BF gas or is isolated from BF gas. It is however preferred to add some BF gas to the incoming gas that is subjected to step (a), in case the BOF gas to be used is relatively lean in $N_2$. Since $N_2$ remains unaffected in step (a), its content in the first product gas originating from step (a) can readily be predicted, such that the skilled person is capable of determining the optimal amount of BF gas to be mixed with the BOF gas in the incoming gas, and no supplementation of BF gas is required downstream of step (a).

It should be noted, however, that the water gas shift reaction of step (a), especially when the incoming gas is rich in BOF gas, affords a first product gas originating from step (a) wherein the $H_2$ to $N_2$ molar ratio is close to 3, typically in the range 2.5-3, or even in the range 2.8-3. In one embodiment, the $H_2$ to $N_2$ molar ratio in the first product gas is about 2.9. Thus, supplementation of the first product gas with $H_2$ is typically not or hardly necessary. The first product gas originating from step (a) is thus ideally suited in the production of ammonia in step (b). In one embodiment, the amount of $H_2$ that is added to the first product gas prior to step (b) is 0-10 mol %, preferably 0-5 mol %, based on the molar content of $H_2$ in the first product gas, wherein 0 mol % refers to the lack of any $H_2$ addition.

The inventors have further found that the $NH_3$ synthesis of step (b) can be further improved by including sorption and regeneration steps. Thus in a preferred embodiment, the $NH_3$ synthesis of step (b) comprises:
 (b1) providing a reaction mixture comprising the first product gas originating from step (a);
 (b2) subjecting the reaction mixture to the equilibrium reaction in a reactor or sequence of reactors, to obtain a reactor outlet mixture comprising the comprising $NH_3$ and at least one of the reactants;
 (b3) regenerating the loaded sorbent obtained in step (b5) by flushing the loaded sorbent with the reactor outlet mixture originating from step (b2), to obtain regenerated sorbent and an effluent comprising desorbed product $NH_3$;
 (b4) separating the effluent originating from step (b3) into a product stream comprising $NH_3$ and a reactant stream comprising $N_2$, $H_2$ and $NH_3$;
 (b5) a sorption step, wherein
  (i) the reactant stream originating from step (b4); and/or
  (ii) an intermediate reactor mixture, which is obtained at the outlet of a reactor not being the last reactor of the reactor sequence, prior to being subjected to the subsequent reactor of the reactor sequence,
 is subjected to an sorption step by contacting with a sorbent selective for $NH_3$, wherein the sorbent is not capable of sorbing $N_2$ and $H_2$, to obtain a sorbent loaded with $NH_3$ and a depleted mixture comprising $N_2$ and $H_2$ that in case step (b5) is performed on the intermediate reactor mixture, is subjected to the subsequent reactor of the reactor sequence.

In one embodiment, the depleted mixture comprising $N_2$ and $H_2$ originating from step (b5) is recycled to the reactor (sequence) of step (b2). In other words, the sorbent of step (b5) is located in the recycle loop. In one embodiment, the depleted mixture comprising $N_2$ and $H_2$ originating from step (b5) is an intermediate reactor mixture, which is subjected to the subsequent reactor in the reactor sequence of step (b2). By virtue of step (b5), the $NH_3$ content in the depleted mixture is reduced. As demonstrated in Example 2, the $NH_3$ synthesis according to this embodiment is greatly improved over conventional $NH_3$ synthesis.

In step (b1), the reaction mixture that is used for the reaction is step (b2) is formed. The reaction mixture comprises at least a product gas originating from step (a), which delivers reactants to the reaction mixture. In a preferred embodiment, the forming of the reaction mixture in step (a) involves mixing the product gas originating from step (a) with a recycle gas, wherein at least part of, preferably all of, the reactant stream originating from step (b4) or the depleted mixture originating from step (b5) is used as recycle gas. The product gas originating from step (a), as referred to in the art as "make-up gas", is the incoming gas for the synthesis of $NH_3$, and contains the reactants of the equilibrium reaction, and may further contain inert compounds. The recycle gas originates from separation step (b4), possibly after sorption step (b5), and contains the reactants of the equilibrium reaction, possibly together with some remaining products of the equilibrium reaction and may further contain inert compounds. The mixing of the two gases may occur upstream of the reactor of step (b2), such that the combined steams, i.e. the reaction mixture, is introduced as such into the reactor, or the mixing may occur inside the reactor of (b2). The volumetric ratio of product gas originating from step (a) to recycle gas may be in the range of 1/99-50/50, preferably in the range of 5/95-30/70, most preferably 7/93-20/80.

In step (b2), the actual equilibrium reaction takes place. The reaction mixture is introduced in a reactor, in which the conditions are such that the reactant(s) is/are partially converted into $NH_3$. Step (b2) may occur in a single reactor or in a reactor sequence. In a preferred embodiment, a reactor sequence is used. A reactor sequence contains at least two sequentially aligned reactors, through which the gaseous mixture is transported. Within the context of the present invention, separate reaction beds within a single larger reactor also classify as a reactor sequence, wherein separate reactors refers the separate stages within the reactor each having a separate reactor bed. A reactor sequence comprises at least two reactors; a first reactor (the upstream reactor) and a last reactor (the downstream reactor). One or more additional reactors may be present in between the first and the last reactor. Preferred reactor sequences have 2-10 reactors, more preferably 2-5 reactors, even more preferably 2 or 3 reactors, most preferably 3 reactors. In case step (b) is performed in a reactor sequence, the reaction mixture is introduced in the first reactor and the reactor outlet mixture is obtained at the outlet of the last reactor. The gaseous mixture that is obtained at the outlet of a reactor that is not the last reactor of the reactor sequence, is herein referred to as "intermediate reactor mixture". The intermediate reactor mixture is introduced in the inlet of the subsequent reactor of the reactor sequence, optionally after an additional step such as step (b5). The conditions within the reactor of step (b2) typically include a temperature of 300-550° C. and a pressure of 150-250 bar. In case a reactor sequence is used, the conditions may vary between the different reactors, such that the equilibrium is pushed as much as possible towards the product(s) during the passage of the reaction mixture through all reactors. The skilled person is acquainted with the use of reactor sequences and knows for which equilibrium reactions the use of reactor sequences is preferred over the use of single reactors. The reactor may contain one or more materials that act as catalyst to facilitate the reaction, i.e. wherein the catalyst is capable of converting $H_2$ and $N_2$ into $NH_3$. Such catalysts are known to the skilled person. As the synthesis of $NH_3$ is exothermic, i.e. the reaction releases energy to the surrounding, typically in the form of heat, the temperature of the outlet of the reactor in step (b2) is higher than the inlet temperature. This higher temperature is advantageously used in step (b3) to regenerate the sorbent by releasing the adsorbed or absorbed product. The high temperature delivers the required heat to drive this endothermic process, as discussed further below for step (b3).

In step (b3), the loaded sorbent is regenerated. In other words, the sorbed species is desorbed from the sorbent such that the sorbent is capable of sorbing further species. The sorption of step (b5) can continue as long as there are sites for sorption available on the sorbent. At some point, the sorbent may become fully saturated with the sorbing species and no further sorption can occur. This is also referred to as break-through. Although step (b5) may continue until break-through (or even beyond, although that would not further improve productivity or yield), the sorbent may also be regenerated before break-through is reached. Sorbent regeneration is known in the art, for example from EP 1344561 and WO 2006/034765. Regeneration typically employs a stripping gas, which is led through the loaded sorbent. Molecules of the stripping gas replace the sorbed $NH_3$ molecules, which are thus desorbed. The desorbed product is obtained as stream at the outlet of the sorbent reactor, e.g. sorbent column. Regeneration of the loaded sorbent is performed with the hot gases exiting the (sequence of) reactor(s), i.e. with the reactor outlet stream. In doing so, the content of ammonia in the reactor outlet mixture rises, as ammonia molecules are desorbed from the loaded sorbent and end up in the effluent gas of the regeneration step. This effluent is then subjected to separation step (b4), typically using a condenser, wherein the target compound is removed as product and the recycle stream containing significant amounts of the target product is subjected to sorption step (b5). As such, both the sorption of step (b5) and the regeneration of step (b3) is conveniently incorporated in existing processes for producing target compounds by equilibrium reactions.

In step (b4), the effluent originating from step (b3) is separated into a product stream comprising ammonia and a reactant stream comprising the reactant(s). Since separation is typically not perfect, the reactant stream will typically still contain ammonia. Difficult separation process between ammonia and hydrogen/nitrogen hampers efficient and complete separation. In a preferred embodiment, the reactant stream is used as recycle and mixed with the feed gas in step (b1), optionally after step (b5). Separation of ammonia is well-known to the skilled person, and any type of separator known in the art may be employed. Step (b4) typically employs a condenser, wherein the effluent originating from step (b3) is cooled such that ammonia is condensed and the reactants remains gaseous, such that the condensed liquid fraction is easily removed from the gaseous fraction. The gaseous compounds are preferably led to the recycle (to step (b1)), preferably via step (b5). Because of the vapour pressure, substantial amounts of ammonia will remain in the gas phase and may thus end up in the recycle. Hence, preferably sorption step (b5) is performed on the reactant stream originating from step (b4). The recycle stream comprising substantial amounts of ammonia would lead to a composition of the stream introduced in the reactor that is closer to the equilibrium and thus a reduced conversion into ammonia.

In step (b5), a mixture of reactants and ammonia is subjected to an sorption step, wherein at least one product of the equilibrium reaction is removed from the mixture by sorption. is contacted with a sorbent material selective for ammonia, meaning that the sorbent remains substantially free from the reactants of the reaction. Further, the sorbent should be capable of sorbing the species to be sorbed, meaning that the sorbent should not be loaded but depleted from sorbed species. In that light, the sorbent to be used in step (b5) may also be referred to as a "lean sorbent", "depleted sorbent" or "regenerated sorbent". If inert compounds are present in the mixture according to step (b5), these inert compounds may either sorb or not sorb to the sorption material, which is irrelevant for the effect of increasing the productivity of ammonia synthesis. The sorption of step (b5) may be adsorption or physisorption, absorption or chemisorption, although adsorption was found to be most preferred. The loaded sorbent is regenerated in step (b3). Selective sorbents for ammonia are known in the art, and may be selected from materials with an intrinsic nanoporous structure, such as molecular sieves and zeolite-like materials (e.g. chabazite, clinoptilotite, mordenite, ferrierite), activated carbon, $MnCl_2$, $NiCl_2$, and $MgCl_2$. In a preferred embodiment, the sorbent is selected from zeolite 3A, 4A, 5A, and 13X.

The ammonia synthesis according to this preferred embodiment thus affords an improved composition for the recycle stream that is reintroduced in the reactor in step (b2). Herein, improved composition refers to a composition that contains a lower amount of ammonia than when step (b5) would not be performed. Relatively, the reaction mixture thus automatically contains higher concentrations of the reactants. The reaction mixture is thus further away from the equilibrium composition, which exits the (sequence of) reactor(s), and thus a higher amount of reactants will be converted into ammonia within the (sequence of) reactor(s). A single pass through the (sequence of) reactor(s) thus gives a higher conversion.

Step (b) affords a product stream comprising ammonia. The product stream originating from step (b) is suitable for the production of urea or ammonium carbamate, especially when combined with the second product stream originating from step (a), which comprises $CO_2$. In the process according to the invention, the product stream originating from step (b) is preferably subjected to step (c).

Step (c): Urea or Ammonium Carbamate Synthesis

The process according to the present preferably involves step (c), wherein urea or ammonium carbamate is synthesized. However, the advantages of the present invention are also obtained in the production of carbon dioxide and ammonia for the production of urea or ammonium carbamate, wherein step (c) is not necessarily present.

The inventors found that the ammonia stream originating from step (b) and the $CO_2$ stream originating from step (a) are ideally suited to be combined and converted into urea or ammonium carbamate in step (c). In the process of the invention, at least part of the $NH_3$ originating from step (b)

and at least part of the $CO_2$ originating from step (a), i.e. from the second product stream originating from step (a), are subjected to step (c). In one embodiment, the process according to the invention is for the production of urea and comprises a step (c) of synthesizing urea. In one embodiment, the process according to the invention is for the production of ammonium carbamate and comprises a step (c) of synthesizing ammonium carbamate. Preferably, the process is for the production of urea.

The conversion of $CO_2$ and $NH_3$ to ammonium carbamate and subsequently to urea is well-known in the art, and occurs through equilibrium reactions (1) for ammonium carbamate, or (1) and (2) for urea:

$$2NH_3 + CO_2 \leftrightarrow H_2NCOONH_4 \qquad (1)$$

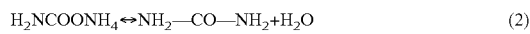

$$H_2NCOONH_4 \leftrightarrow NH_2-CO-NH_2 + H_2O \qquad (2)$$

The synthesis of urea and ammonium carbamate from $CO_2$ and $NH_3$ is known to the skilled person, and the exact conditions and parameters of step (c) are not crucial for the operation of the process according to the invention. Typically, for the synthesis of urea, step (c) operates at a temperature of 100-300° C. preferably 150-250° C. most preferably 170-200° C. and a pressure of 100-500 bar, preferably 100-200 bar, most preferably 120-170 bar. Typically, for the synthesis of ammonium carbamate, step (c) operates at a temperature of 0-40° C., preferably 10 to 30° C. and a pressure of 1 to 10 bar.

In step (c), $NH_3$ and $CO_2$ are used in a molar ratio of 2. However, due to complex azeotropic physical phase equilibria, the molar ratio of $NH_3$ to $CO_2$ in the feed of step (c) is optimally in the range of 2 to 4, more preferably 2.5 to 3.5 and most preferably 2.5 to 2.6. The amount of $CO_2$ present in the second product stream originating from step (a) is typically too high for the amount of $NH_3$ present in the product stream of step (b), and thus all of the $NH_3$ originating from step (b), or in other words as present in the product stream of step (b), is used in step (c), and the amount of $CO_2$ as comprised in the second product stream originating from step (a) that is used in step (c) is adjusted thereto. Thus, in a preferred embodiment, the $NH_3$ originating from step (b) and at least part of the $CO_2$ originating from step (a) is subjected to step (c). Preferably, 10-50%, more preferably 20-30%, of the second product stream originating from step (a), based on total moles $CO_2$, is used in step (c). The remaining of the second product stream originating from step (a) is not used in step (c) and may be considered a waste stream or used as deemed fit. This stream is advantageously subjected to carbon sequestering, since it is obtained as a concentrated $CO_2$ stream and as a single off-gas from the process according to the invention. As such, carbon sequestering is readily performed on the left-over second product stream of step (a).

The urea or ammonium carbamate produced in step (c) may be considered the main product of the process according to the present embodiment, wherein step (c) is performed. It may be used as deemed fit, such as in fertilizers or converted into further useful compounds.

EXAMPLE

Example 1: SEWGS

A computational experiment is performed, wherein BOF gas (total 528 kmol) and steam (599 kmol) is subjected to a pre-shift and subsequent sorption-enhanced water gas shift (SEWGS), with an overall conversion of 99%, based on CO. The SEWGS operates with 100% recovery of $H_2$ and $N_2$ and 99% recovery of $CO_2$. The SEWGS off-gas (first product gas) is subjected to methanation and subsequent condensation to remove $CH_4$. After methanation, the first product gas contains 100 kmol $N_2$ and 289 kmol $H_2$. 11 kmol $H_2$ is added to the first product gas, to obtain a $H_2$ to $N_2$ molar ratio of 3. This gas is subjected to ammonia synthesis to afford 200 kmol $NH_3$. The second product gas, obtained by sorbent regeneration after SEWGS, is rich in $CO_2$. For the production of urea, all of the product gas of the $NH_3$ synthesis can be used together with 100 kmol of $CO_2$ from the second product stream. The remainder of the $CO_2$ may be subjected to $CO_2$ sequestering. The composition of the relevant gaseous mixtures is provided in Table 1.

TABLE 1

Composition of starting material, intermediate and product compositors (in kmol)

| | $N_2$ | $H_2$ | CO | $CO_2$ | $CH_4$ | $NH_3$ |
|---|---|---|---|---|---|---|
| BOF gas | 100 | 18 | 300 | 110 | 0 | 0 |
| Product gas of pre-shift | 100 | 287 | 30 | 379 | 0 | 0 |
| First product gas of SEWGS | 100 | 314 | 4 | 3 | 0 | 0 |
| First product gas after methanation | 100 | 289 | 0 | 0 | 7 | 0 |
| Product gas of $NH_3$ synthesis | 0 | 0 | 0 | 0 | 0 | 200 |
| Second product gas of SEWGS | 0 | 0 | 0 | 403 | 0 | 0 |

Example 2: Ammonia Synthesis

This example evidences the beneficial effects of the ammonia synthesis according to the preferred embodiment, involving steps (b1)-(b5). During conventional ammonia synthesis, the incoming gas of the ammonia reactor (for step (b2)) contains about 90 vol % of a recycle and only 10 vol % of feed gas, containing the reactants. The recycle gas contains about 5 wt % ammonia, leading to a 4 wt % ammonia concentration of the gas that is introduced in the reactor. The equilibrium is established at about 13 wt % ammonia, such that only about 8.5 wt % ammonia is formed in a single pass through the reactor. The reactor outlet mixture containing 13 wt % ammonia is conventionally led to the condenser, where ammonia is separated and a recycle stream is formed, which contains about 5 wt % ammonia. In an especially preferred embodiment of the process according the invention, the reactor outlet stream, typically containing about 13 wt % ammonia, is first used as stripping gas to regenerate a sorbent loaded with ammonia in step (b3). This leads to an increase of the ammonia concentration to about 20 wt %. This effluent of the regeneration step is led to the condenser, where ammonia is condensed and separated as a product stream. Again, a recycle containing about 5 wt % ammonia is formed, but in view of the higher ammonia concentration in the incoming stream entering the condenser, the amount of ammonia in the product stream is higher. Then, the recycle containing about 5 wt % ammonia is subjected to sorption step (b5), where ammonia is sorbed to the sorbent such that the effluent of the sorption step contains only about 1 wt % ammonia. This gas is used for the recycle, such that the amount of ammonia that is introduced in the reactor is advantageously reduced from about 5 wt % to about 1 wt %. A single pass through the reactor in the process of the invention thus allows the formation of about 16 wt % ammonia. A further effect is that the recycle is smaller, meaning that about 85 vol % of the recycle can supplemented with 15 vol % of feed gas to be introduced in the reactor. The increased yield within the reactor combined with the additional ammonia that is removed from the recycle and collected during regeneration gives a yield increase from 11 wt % to about 19 wt %. Such a marked increase is obtainable with the process according to the invention, which does not require any adaptations on the reactor or the catalyst that is been used, but is purely the results of an intermediate sorption/regeneration step.

The inventors demonstrated the effect of introducing a sorption step according to preferred embodiment of step (b), as is shown in the table below, wherein Conv. refers to the conventional process as outlined above, and Emb. 1-4 refer to four embodiments according to the present invention. All processes contain a sequence of three reactors wherein ammonia is formed (pressure=100 bar), and a condenser (pressure=5 bar; T=5° C.) which is used to condense all ammonia, except for the 5 wt % of ammonia that remains in the vapour phase. Further, all processes employ a heat exchanger for heating the reaction mixture of feed gas and recycle gas and cooling the reactor outlet gas (after the regeneration step if present). In Emb. 1-4, the catalyst used is any conventional catalyst for ammonia production, e.g. an iron-based catalyst or a ruthenium-based catalyst, and the concentration of $NH_3$ at the outlet of reactor 3 is based on the outlet temperature chosen. Establishing the outlet temperature, based on the intermediate cooling in place and the concentration of $NH_3$ in the feed, is well-known in the art.

synthesis can be reduced, because the kinetics of the ammonia conversion are increased by higher temperature.

A similar set of experiments was performed for higher reactor pressure (200 bar) and lower or higher condenser temperature (−5° C. or 30° C.). The resulting single pass conversions are shown in the table below:

|  | Conv. 2 | Emb. 5 | Emb. 6 | Emb. 7 |
| --- | --- | --- | --- | --- |
| Sorption between reactor 1 and 2? | NO | NO | NO | NO |
| Outlet T of reactor 3 (° C.) | 450 | 450 | 450 | 480 |
| Regeneration after reactor outlet? | NO | YES | YES | YES |
| Condenser T (° C.) | −5 | −5 | 30 | 30 |
| Condenser pressure (bar) | 3.5 | 3.5 | 10 | 10 |
| Sorption after condenser? | NO | YES | YES | YES |
| single pass conversion (%) | 22.8 | 24.7 | 27.1 | 22.8 |

Increasing the reactor and lowering the condenser temperature (Conv. 2 vs. Conv. 1) is known to increase the single pass conversion. Even at such conditions, the process according to the invention was capable of further increasing the single pass conversion, from 22.8% to 24.7%. Remarkably, operating the condenser at less stringent conditions (T=30° C.) even increased the single pass conversions for the inventive process, because the $NH_3$ content is increased during regeneration, and thus there is more $NH_3$ to condense.

|  | Conv. 1 | Emb. 1 | Emb. 2 | Emb. 3 | Emb. 4 |
| --- | --- | --- | --- | --- | --- |
| feed gas / recycle gas (v/v) | 8.5/91.5 | 13/87 | 15.5/84.5 | 8.5/91.5 | 13/87 |
| [$NH_3$] at inlet of reactor 1 (wt %) | 4.5 | 0.85 | 0.85 | 0.9 | 4 |
| Sorption between reactor 1 and 2? | NO | NO | NO | NO | YES |
| [$NH_3$] at outlet of reactor 1 (wt %) | n/a | n/a | n/a | n/a | 10 |
| [$NH_3$] at inlet of reactor 2 (wt %) | n/a | n/a | n/a | n/a | 3 |
| [$NH_3$] at outlet of reactor 3 (wt %) | 13 | 10 | 13 | 5.7 | 13 |
| Outlet T of reactor 3 (° C.) | 450 | 480 | 450 | 550 | 450 |
| Regeneration after reactor outlet? | NO | YES | YES | YES | YES |
| [$NH_3$] after regeneration (wt %) | n/a | 13.8 | 16.5 | 9.4 | 19.5 |
| [$NH_3$] in recycle after condenser (wt %) | 5 | 5 | 5 | 5 | 5 |
| Sorption after condenser? | NO | YES | YES | YES | NO |
| [$NH_3$] in recycle after sorption (wt %) | n/a | 1 | 1 | 1 | n/a |
| single pass conversion (%) | 8.5 | 12.9 | 15.6 | 8.5 | 12.9 |

At similar reactor outlet temperatures, the single pass conversion could be increased from 8.5% (conventional process) to 15.6% (inventive process, option (i)) or 12.9% (inventive process, option (ii)). Emb.1 shows that even with a higher outlet temperature of the final ammonia synthesis reactor, which lowers the $NH_3$ concentration at that point, compared to the conventional process, the single pass conversion could still be increased. Emb. 1 represents the situation wherein the same heat exchange network within the reactor sequence is in place as for the conventional case. Emb. 2 shows that when the temperature of the outlet of the final ammonia conversion reactor is kept the same, i.e. the heat exchange network within the reactor sequence is upgraded compared to the conventional process, the single pass conversion can almost be doubled. Emb. 3 shows that the outlet temperature can be allowed to reach much higher temperatures compared to the conventional process, which drives the concentration of $NH_3$ in the reactor outlet mixture down from 13 vol % to 5.7 vol %, while keeping the same single pass conversion. In this embodiment, the heat exchange network between synthesis reactors is relaxed, compared to the conventional process. A higher reactor outlet temperature, and thus a higher overall reaction temperature, means that the size of the reactor for the ammonia

The invention claimed is:

1. A process for the production of carbon dioxide and ammonia for the production of $H_2NC(O)X$, wherein $X=NH_2$ or $O^- NH_4^+$, comprising:
   (a) subjecting a mixture comprising (i) basic oxygen furnace gas and (ii) steam to a separation-enhanced water gas shift reaction to obtain a first product gas comprising $H_2$ and $N_2$ and a second product gas comprising $CO_2$;
   (b) subjecting the first product gas originating from step (a) to $NH_3$ synthesis to obtain a product gas comprising $NH_3$; and
   (c) optionally subjecting at least part of the $CO_2$ originating from step (a) and at least part of the $NH_3$ originating from step (b) to the synthesis of $H_2NC(O)X$,
   wherein the $H_2$ to $N_2$ ratio in the first product gas originating from step (a) is in a range of 2.5 to 3.

2. The process according to claim 1, wherein the process is for the production of $H_2NC(O)X$ and wherein step (c) is performed.

3. The process according to claim 2, wherein the molar ratio $NH_3$ to $CO_2$ in step (c) is in the range of 2-4.

4. The process according to claim 3, wherein all of the $NH_3$ originating from step (b) and part of the $CO_2$ originating from step (a) is used in the feed of step (c).

5. The process according to claim 1, wherein the $H_2$ to $N_2$ molar ratio in A the first product stream that is subjected to step (b) is set to 3 by addition of $H_2$.

6. The process according to claim 5, wherein 0-10 mol % $H_2$ is added to the first product gas prior to step (b), based on the molar content of $H_2$ in the first product gas.

7. The process according to claim 1, wherein the remainder of the second product gas originating from step (a) is subjected to $CO_2$ sequestering.

8. The process according to claim 1, wherein $X=NH_2$.

9. The process according to claim 1, wherein in case the first product gas originating from step (a) comprises CO and $CO_2$, it is subjected to methanation to convert CO and $CO_2$ into $CH_4$, prior to being subjected to step (b).

10. The process according to claim 1, wherein a pre-shift step is performed prior to step (a), wherein the mixture is subjected to a water gas shift reaction that is not separation-enhanced before being subjected to step (a).

11. The process according to claim 1, wherein step (a) involves:
   (a1) contacting the incoming gas with a sorbent capable of adsorbing $CO_2$, under conditions suitable to convert CO and $H_2O$ in $H_2$ and $CO_2$, to obtain a first product gas comprising $H_2$ and $N_2$, and a sorbent loaded with $CO_2$; and
   (a2) regenerating the loaded sorbent to obtain a second product gas comprising $CO_2$.

12. The process according to claim 1, wherein the electricity needed to perform the process is obtained from renewable resources.

13. The process according to claim 1, wherein step (b) involves:
   (b1) providing a reaction mixture comprising the first product gas originating from step (a);
   (b2) subjecting the reaction mixture to an equilibrium reaction in a reactor or sequence of reactors, to obtain a reactor outlet mixture comprising $NH_3$ and at least one of the reactants;
   (b3) regenerating the loaded sorbent obtained in step (b5) by flushing the loaded sorbent with the reactor outlet mixture originating from step (b2), to obtain regenerated sorbent and an effluent comprising desorbed product $NH_3$;
   (b4) separating the effluent originating from step (b3) into a product stream comprising $NH_3$ and a reactant stream comprising $N_2$, $H_2$ and $NH_3$;
   (b5) a sorption step, wherein
      (i) the reactant stream originating from step (b4); and/or
      (ii) an intermediate reactor mixture, which is obtained at the outlet of a reactor not being the last reactor of the reactor sequence, prior to being subjected to the subsequent reactor of the reactor sequence,
   is subjected to a sorption step by contacting with a sorbent selective for $NH_3$, wherein the sorbent is not capable of sorbing $N_2$ and $H_2$, to obtain a sorbent loaded with $NH_3$ and a depleted mixture comprising $N_2$ and $H_2$ that in case step (b5) is performed on the intermediate reactor mixture, is subjected to the subsequent reactor of the reactor sequence.

14. The process according to claim 1, wherein the mixture that is subjected to a separation-enhanced water gas shift reaction in step (a) consists of (i) basic oxygen furnace gas and (ii) steam.

* * * * *